United States Patent
Adler

(10) Patent No.: US 6,690,010 B1
(45) Date of Patent: Feb. 10, 2004

(54) CHEMICAL ANALYSIS OF DEFECTS USING ELECTRON APPEARANCE SPECTROSCOPY

(75) Inventor: David L. Adler, San Jose, CA (US)

(73) Assignee: KLA-Tencor Technologies, San Jose, CA (US)

( * ) Notice: Subject to any disclaimer, the term of this patent is extended or adjusted under 35 U.S.C. 154(b) by 0 days.

(21) Appl. No.: 09/396,548

(22) Filed: Sep. 2, 1999

Related U.S. Application Data

(60) Provisional application No. 60/099,117, filed on Sep. 3, 1998.

(51) Int. Cl.[7] ................................................. H01J 37/26
(52) U.S. Cl. ...................... 250/310; 250/305; 250/306; 250/307; 250/311; 250/397; 378/44; 378/45; 364/497; 364/498
(58) Field of Search ................................ 250/307, 310, 250/305, 306, 311, 397; 378/45, 44; 364/497, 498

(56) References Cited

U.S. PATENT DOCUMENTS

| | | | |
|---|---|---|---|
| 4,877,326 A | | 10/1989 | Chadwick et al. |
| 5,142,149 A | | 8/1992 | Isakozawa et al. |
| 5,315,113 A | * | 5/1994 | Larson et al. ............... 250/305 |
| 5,369,275 A | * | 11/1994 | Usui et al. ................... 250/310 |
| 5,393,977 A | | 2/1995 | Okura et al. |
| 5,430,786 A | * | 7/1995 | Komatsu et al. ............... 378/45 |
| 5,594,246 A | * | 1/1997 | Sudo et al. ................... 250/310 |
| 5,635,716 A | * | 6/1997 | Liu et al. ..................... 250/310 |
| 5,703,361 A | | 12/1997 | Sartore |
| 5,869,833 A | | 2/1999 | Richardson et al. |
| 5,973,323 A | | 10/1999 | Adler et al. |

OTHER PUBLICATIONS

Robert L. Park, et al., Appearance Potential Spectroscopy on an Austere Budget, Letters to the Editor, Surface Science 26, pp. 664–666 (1971).

D. R. Chopra, et al., Appearance Potential Spectroscopy of Solid Surfaces, Scanning Microscopy, vol. 2, No. 2, pp. 677–702 (1988).

* cited by examiner

Primary Examiner—John R. Lee
Assistant Examiner—Zia R. Hashmi

(57) ABSTRACT

A technique for measuring the chemical composition of surface particles or other small features which may be present on semiconductor wafers or other substrates. A particle is irradiated with a variable energy, focused incident electron beam. X-ray or electron emissions from the particle are monitored to detect an increase in output indicating the ionization threshold of the materials in the particle. The incident beam energy is correlated with the thresholds detected to determine the species present in the particle.

51 Claims, 6 Drawing Sheets

CHEMICAL ANALYSIS OF DEFECTS USING ELECTRON APPEARANCE SPECTROSCOPY

This application claims the benefit of Provisional application No. 60/099,117, filed Sep. 3, 1998.

BACKGROUND OF THE INVENTION

The present invention relates generally to a method for determining the chemical composition of fine features, such as surface particles on semiconductor wafers. During the manufacturing test of semiconductor wafers, the location of small defects may be detected using a variety of methods. Frequently, the composition of the defect yields important information about the manufacturing process. Such information may assist, for example, in isolating problems in the manufacturing process or discovering contamination from errant debris in the manufacturing environment.

Others have proposed determining the composition of small defects using "energy-dispersive spectroscopy", or EDS, as described in relation to FIG. 1. In an EDS system 10, an incident electron beam 20 is directed towards a known defect location 22 at a fixed energy, generally 5–20 keV. X-rays 24 are emitted from the defect particle and detected by an x-ray detector 30. Chemical identification of a defect is made by resolving the energy of x-rays emitted from the sample as a result of the irradiation.

The incident beam 20 in EDS system 10 has a fixed energy and current, and all of the x-rays emitted by the sample are detected simultaneously by detector 30 and their energies are resolved. X-ray emissions occur only when the incident electron energy exceeds a minimum threshold energy level sufficient to knock electrons out of particular levels. FIG. 2 shows a diagram plotting the intensity of the x-rays detected by detector 30 across x-ray energies for a sample including aluminum (Al), silicon (Si), copper (Cu) and tungsten (W), all commonly used in the manufacture of semiconductor devices. Around the x-ray energy level of Al a peak intensity 50 indicates an increased level of x-rays emitted from the sample location. Similarly a peak intensity 54 is indicated around the energy level of Cu.

A smaller intensity peak 52 is formed around the area of energy level of Si. The difference between the x-ray energy level of Al and Si is only about 250 eV. Because the resolving power of the detectors used in EDS is never better than 50 eV, and is frequently worse than 150 eV, a great deal of data must be collected in order to resolve two peaks so close together.

EDS systems also present another problem. For most atomic species, the 5–20 keV supplied by the incident beam 20 of an EDS system is much greater than that necessary to excite the electrons, so the depth of material probed is usually 0.5 to 5 microns. However, a small defect particle may be as little as 0.1 microns deep. For a small defect particle 22, as shown in FIG. 1, the beam may therefore probe the substrate 12 as well as the defect 22. As beam 20 penetrates the substrate 12, the electrons of the beam are deflected throughout a volume 26, that may be 1–10 microns wide, exciting other electrons in the volume. X-rays 28 are emitted from atoms throughout the probed volume. It is impossible to discern between the x-rays emitted from the particle or from the substrate, so it cannot be determined if any chemicals detected are from the errant particle, or are from the substrate. Some have solved this problem by testing at the particle location, and testing a second time near the particle area to resolve the difference, but this process requires additional processing time and may introduce other errors if the neighboring area tested has different structures from the defect area.

Another technique that has been used by others to determine the chemical composition of defects is Auger Electron Spectroscopy (AES), illustrated by system 70, shown in FIG. 3. In an AES process, a fixed electron beam 72 of 3–5 keV is projected towards particle 22 on substrate 12. Auger electrons 74 are emitted from particle 22 and detected by an electron energy analyzer 76. The energy of Auger electrons is well known, and is fixed for each atomic species.

Although the beam 72 may penetrate the particle 22 and substrate 12, Auger electrons, unlike x-rays, are only released from the surface area struck by the beam. An AES system effectively probes only about 0.005–0.05 microns into the particle. Although this solves the problem in EDS of probing the substrate below the defect particle, it raises additional implementation problems. Since such a shallow amount of the surface is probed, it is very important that the surface is not contaminated with even a minute residue of other material. For example, condensed water in the air will affect the chemical determination. This problem has been reduced by cleaning the surface by ion-bombardment 82, and holding the material in an ultra-high vacuum chamber 80 at $10^{-9}$ Torr or lower before measurements are made.

The specialized equipment needed for AES systems—ultra high vacuum system and electron energy analyzer—is very expensive, and requires highly-trained operators. Auger systems, because of the need for ultra-high vacuum control, also cannot be easily retrofit to existing manufacturing equipment. AES is therefore not suitable for in-line analysis of semiconductor product wafers, and is instead commonly used for failure analysis of semiconductor devices.

A third method employs variations of electron appearance spectroscopy to the problem of identifying materials. For example, Park and Houston, in "APPEARANCE POTENTIAL SPECTROSCOPY ON AN AUSTERE BUDGET", SURFACE SCIENCE, 26 (1971) (pages 664–666), Letters to the Editor, describe a simple appearance spectroscopy system in which the derivative of the photocurrent as a function of the sample potential exhibits sharp peaks at the potentials corresponding to the threshold energies. Chopra and Chourasia in "APPEARANCE POTENTIAL SPECTROSCOPY OF SOLID SURFACES" SCANNING MICROSCOPY, Vol. 2, No. 2, 1988 (pages 677–702), review appearance spectroscopy and survey some applications.

These and other works in appearance spectroscopy are based upon a simple spectrometer employing a tungsten filament which provides electrons which impinge on the sample to be studied. A grid electrically separates the filament and the detector assembly, and x-rays passing through the grid strike the walls of the chamber. The resulting photoelectrons are collected on a positive electrode. The resulting signal is amplified and synchronously detected by a phase-lock amplifier.

Previous work in appearance spectroscopy, however, has failed to consider a focused electron beam projected towards particular locations on the specimen, but instead found the properties of materials over large areas.

SUMMARY OF THE INVENTION

In accordance with the purpose of the invention, as embodied and broadly described herein, the invention comprises a method of and an apparatus for determining the chemical composition of a feature on a substrate, comprising the steps of directing a focused electron beam towards the feature, thereby causing the feature to emit x-rays, detecting x-rays emitted from the feature, while varying the energy of the beam and maintaining the focus of the beam on the feature, and determining the composition of the feature. The electron beam may be scanned over a surface of the substrate or stepped over the surface of the substrate to locations corresponding substantially to predetermined defect sites on the substrate.

The method may additionally comprise sequentially directing the focused electron beam towards each of a plurality of features on the substrate, sequentially detecting x-rays emitted from each of the features while varying the energy of the beam, and determining the composition of each of the features. The composition of the feature may be determined by monitoring the relative intensity of the x-rays while varying the energy of the beam. The energy may be gradually increased while the x-rays are detected. The composition of the feature can be determined from a lock-in signal corresponding to a derivative of the intensity of the x-rays. The use of lock-in detection as described herein includes, without limitation, those methods described on pages 460–461 of "Building Scientific Apparatus" (Second Edition) by Moore el al., published in 1989 by Addison Wesley, the description of which is incorporated herein by reference. Other averaged forms of detection may also be used.

The beam may be sequentially varied through predetermined energy levels selected to produce an increase in x-ray emission intensity from known materials. The substrate may be maintained at a substantially constant voltage, preferably of about zero volts, for example by a gas jet directed at the substrate. Alternatively, an electron beam, preferably a de-focused electron beam having a very low landing energy, may be used to maintain the substrate at a substantially constant voltage.

Another aspect of this invention is a method for determining the chemical composition of a feature, comprising directing a focused electron beam towards the feature, the electron beam having a predetermined energy corresponding to a value which causes an element to emit electrons, detecting electrons emitted from the feature, while varying the energy of the beam in a range around the predetermined energy and while maintaining the focus of the beam on the feature, and determining the composition of the feature.

A further aspect of this invention is an apparatus for determining the chemical composition of a feature on a substrate, comprising: a means for directing a focused electron beam towards the feature, thereby causing the feature to emit x-rays; a means for detecting the x-rays emitted from the feature, while varying the energy of the beam and maintaining the focus of the beam on the feature; and a means for determining the composition of the feature. The means for directing the focused electron beam may include an electron gun or other system for producing electrons, and focusing electronics, which may include software or hardware which is used to control the focus of the beam while varying its energy. The means for detecting x-rays may include any suitable x-ray detector, such as a scintillator or any other solid state semiconductor detector. The means for determining the composition of the feature may include software or hardware, such as a programmed processor (with or without additional memory) or a hardwired system, to analyze the data from the detector.

Still another aspect of this invention is an apparatus for determining the chemical composition of a feature on a substrate, comprising: a means for directing a focused electron beam towards the feature, thereby causing the feature to emit electrons; a means for detecting the electrons emitted from the feature, while varying the energy of the beam and maintaining the focus of the beam on the feature; and a means for determining the composition of the feature. The means for directing the focused electron beam may include an electron gun or other system for producing electrons, and focusing electronics, which may include software or hardware which is used to control the focus of the beam while varying its energy. The means for detecting emitted electrons may include a channeltron, an anode, or a system which measures current at the sample. The means for determining the composition of the feature may include software or hardware, such as a programmed processor (with or without additional memory) or a hardwired system, to analyze the data from the detector.

Objects and advantages of the invention will be set forth in part in the description which follows and in part will be obvious from the description or may be learned by practice of the invention. The objects and advantages of the invention will be realized and attained by means of the elements and combinations particularly pointed out in the appended claims.

BRIEF DESCRIPTION OF THE DRAWINGS

The accompanying drawings, which are incorporated in and constitute a part of this specification, illustrate several embodiments of the invention and, together with the description, serve to explain the principles of the invention.

DETAILED DESCRIPTION

Figure 1:
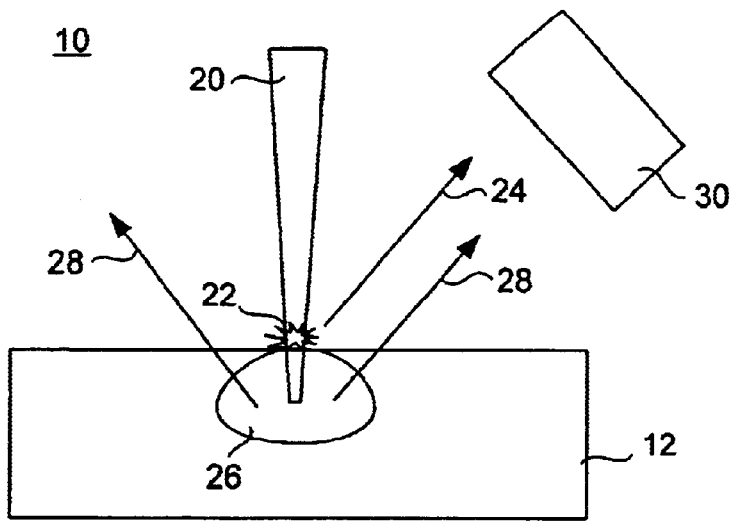
FIG. 1 illustrates the use of "energy-dispersive spectroscopy" (EDS) techniques of the prior art.
Figure 2:
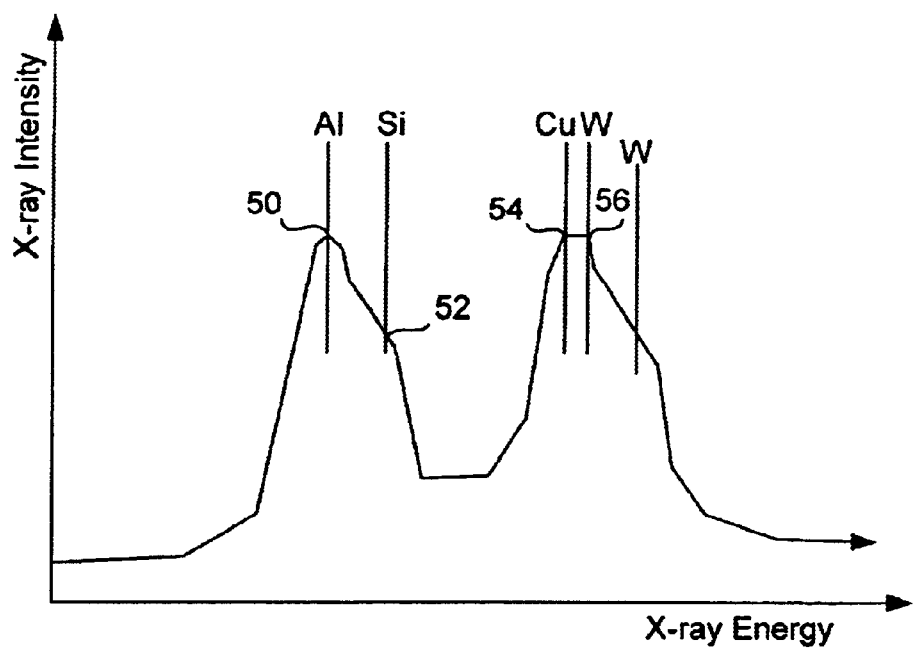
FIG. 2 shows a diagram plotting the intensity of the x-rays across incident beam energies.
Figure 3:
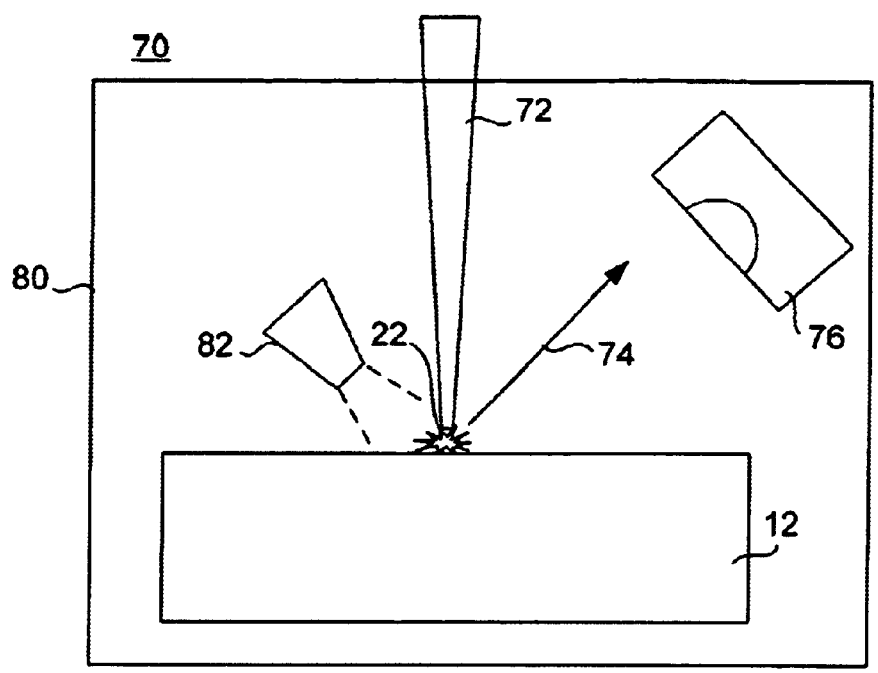
FIG. 3 illustrates the use of "Auger Electron Spectroscopy" (AES) techniques of the prior art.

Reference will now be made in detail to the preferred embodiments of the invention, examples of which are illustrated in the accompanying drawings.

The present invention uses Electron Appearance Spectroscopy (EAS) to determine the chemical composition of defect particles, solving many of the problems associated with EDS and AES systems. In an EAS system 90, shown in FIG. 4, a variable energy, focused electron beam 92 is projected towards particle 22. The position of the beam is fixed on the particle during this step, and the beam current is maintained at an approximately constant value. The beam energy may be varied continuously, or in a step-wise manner. X-rays 94 are detected by a detector 96, which measures the intensity of the x-rays.

As discussed above, emissions from atomic species are extremely sensitive to the incident electron beam energy, so x-ray emissions occur only when the incident beam reaches an energy level sufficient to excite electrons out of particular levels. Below a certain energy, the excitation "threshold", there is no x-ray emission from a specific element. However, above the threshold, x-rays are emitted from a small volume near the surface. Just as the difference in the energy levels is specific to each element, this threshold energy level is unique for each atomic element. By monitoring the x-ray emission from a particular sample area as the electron beam energy is varied over a range of energies (which may correspond to known threshold energies for elements of interest), the elements present in the sample with excitation thresholds in that range of energies can be detected. This technique is known as "appearance spectroscopy".

Figure 5:
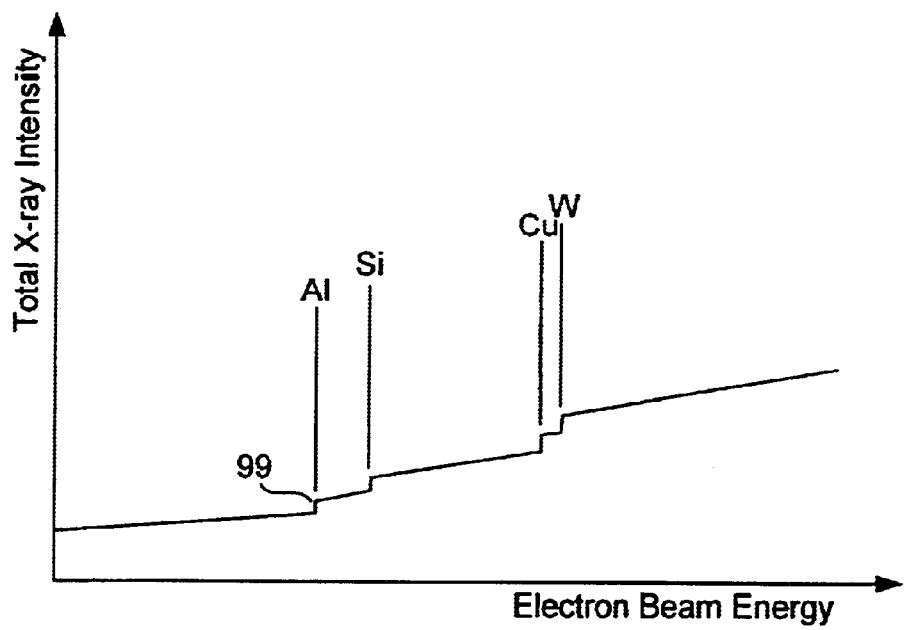
FIG. 5 shows the total x-ray intensity output produced as a result of the incident electron beam energy.

As shown in FIG. 5, the total x-ray intensity output produced by a specimen increases sharply at the point at which the incident electron beam energy reaches the threshold energy of a particular species. Atomic species are detected using the very sharp increase in output at the threshold energy of the electron beam. As seen in FIG. 5, the output signal increases dramatically when the incident beam reaches threshold energy 99, indicating that Aluminum is present in the particle being inspected. The incident electron beam energy may be known to a fraction of a volt, leading to a clear resolution between elements. Thus, it is possible to differentiate neighboring elements such as Cu and W, even at low energies, by detecting the incident beam energy required to produce the signal increase at the threshold energy.

Figure 6:
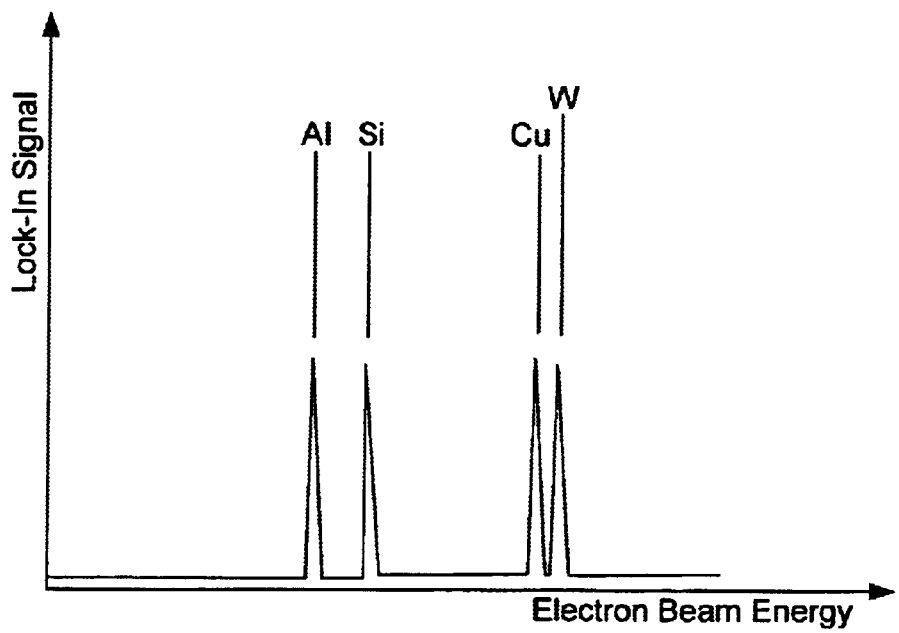
FIG. 6 shows the results of lock-in signal processing of the output signal shown in FIG. 5.

The resolution of threshold voltages may be determined to about 5 volts or less in an EAS system, compared with 50–150 eV in EDS. The signal may further be greatly enhanced by using a lock-in detection scheme, which in effect measures the derivative of the energy signal. As shown in FIG. 6, the lock-in signal provides sharp signal changes at the threshold energies of the materials present in the sample. Lock in is accomplished by dithering the incident energy by a small amount at high frequency. The output x-ray or electron signal at the same frequency is synchronously detected. This also has the advantage of improving the signal to noise ratio.

In the present invention, the electron beam is focused while varying its energy through a predetermined range of energies, so that the materials present at specific locations may be determined. In one aspect of the present invention, appearance spectroscopy uses the x-rays produced by a sample irradiated with a variable focused incident electron beam to determine the atomic species present at a particular location by detecting the incident beam energy necessary to produce an increased x-ray output signal. It can be seen that the techniques of the present invention using focused electron beam electron appearance spectroscopy solves many of the problems which are present in previous materials identification systems.

In prior EDS systems the incident beam energy is fixed, and chemical identification is made by resolving the energy of the emitted x-rays, and the resolution of atomic species can only be resolved at the resolution of the detector. With this poor energy resolution, it is often difficult to differentiate between different chemical species in the sample. The EAS system of the present invention solves this problem by detecting the output threshold energy.as the incident beam varies over a range of energies, noting the increases in intensity of the output signal without necessarily resolving the output energy signal.

The second advantage of the technique of the present invention is in the volume of the sample probed. Since EDS relies on a beam with fixed energy much higher than the threshold energy, the depth probed is usually 0.5 to 5 microns. At this depth, the beam penetrates the substrate, making it impossible to discern between the substrate and an errant silicon particle, for example. The high energy of the beam also causes the incident electrons to excite other electrons and produce x-rays from a wide lateral volume in the substrate. Alternately, AES systems effectively detect only auger electrons emitted from the particle surface 0.005–0.05 microns deep, and so require sample cleaning prior to measurement to ensure that the particle surface is not contaminated.

In the present invention, however, the minimum energy of the incident beam, just above the threshold energy, is used to detect each species. The resulting x-ray output intensity levels from the particle is detected. The incident beam probes a very small volume of the particle, ranging from 0.01 to 0.1 microns deep, depending on the material and its threshold energy. Furthermore, the lateral volume probed is limited to approximately the width of the incident beam.

A further advantage of the present invention is that the proposed technique minimizes electron beam damage to the sample by using the lowest possible beam energy. Electron beams can introduce damage to wafers due to heating and the generation of "hot electrons" and static charge in the gate region. By using the lowest possible incident beam energy, these effects are greatly reduced. This helps to make the present invention suitable for in-line inspection of product semiconductor wafers, and other materials susceptible to damage by the incident electron beam.

The proposed technique may also be considerably faster than EDS or AES systems, since it is possible to restrict the variation of the beam energy only to those threshold values for species considered likely to be present in the sample. If, for example, only Al and W need be detected in a Si sample, then the beam energy can be varied over only the Al and W threshold energies. In EDS and AES systems, the incident beam energy is fixed, and the resulting output signal must be detected over a large range of output energies to compile enough data to resolve closely located atomic species.

Figure 4:
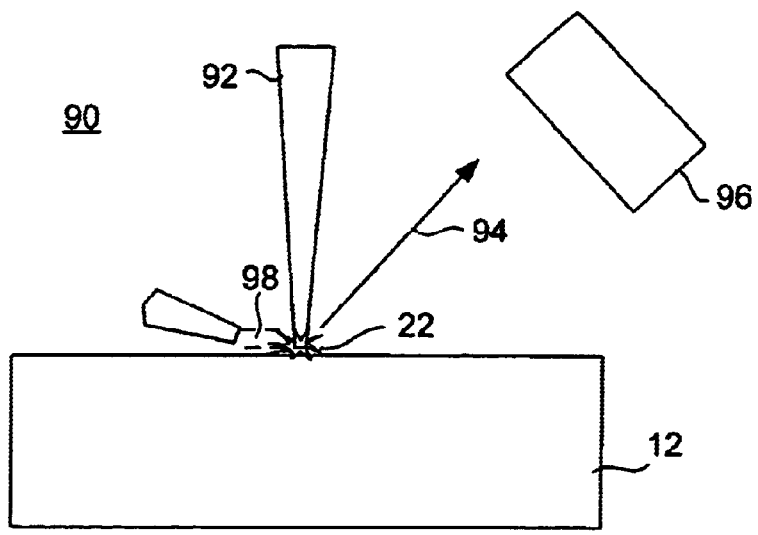
FIG. 4 illustrates the use of "Electron Appearance Spectroscopy" techniques of the present invention.
Figure 7:
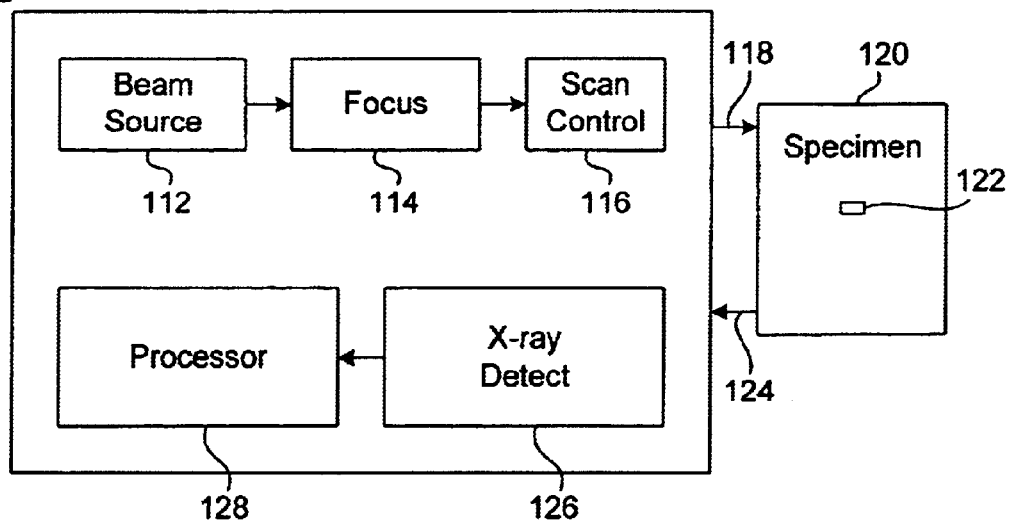
FIG. 7 shows a block diagram of a system using the techniques of the present invention.

FIG. 7 shows a block diagram of a system 110 which uses the techniques of the present invention as shown and discussed in relation to FIG. 4. A beam source 112, a focus controller 114, and beam energy controller 116 direct the variable energy, focused electron beam towards particular locations 122 on specimen 120. X-ray detecting means 126 detects x-rays 124 emitted from specimen 120. In the system of the present invention, x-ray detecting means 126 may be a simple device which senses an increase in x-ray emission intensity at any given incident beam energy without need to resolve the energy of the x-rays. The x-ray signal is processed by processor 128. Processor 128 may be used to control the lock-in detection scheme. The processor 128 also can be used to compare the electron beam energy values corresponding to a sensed increase in detected x-ray output with known energy values stored in a look-up table, and thereby identify the composition of the sample from the known energy values. The processor may be a programmable general purpose microprocessor, hardwired logic in an ASIC, or any other suitable system for processing the required data at a sufficient rate.

Electron beam 118 is projected by focus 114 and controller 116 towards a defect location 122. The location of the defect may be determined by any of many well-known defect location techniques. In a preferred embodiment, the defects are initially located in a separate apparatus by optical techniques. The locations of these defects are stored in a computer file, and this information is transferred to the system of the present invention, which relocates the defects and determines their composition. The defects may be relocated, at least in part, by an operator viewing an image of the sample on a CRT screen or the like.

Electron beam source 112 is a variable source that can be controlled over a wide range of energy levels by controller 116. Focus control 114 is used to keep the beam in focus as its energy is varied. Focus control 114 may be implemented under computer control to keep beam 118 focused as it varies across a range of 1–5 keV, and more preferably across a range of about 1–3 keV.

X-ray detector 126 detects an increase in the level of output x-rays. It is not necessary for the x-ray detector 126 to resolve the output energy. Detector 126 may be a PIN-diode, a scintillator, or any other suitable detector. The energy of the incident beam is correlated by processor 128 with the intensity of the output signal from x-ray detector 126. This information may be used to determine when the incident beam has reached a threshold energy level. By determining the energy level of each threshold, the chemical composition of the particle being inspected can be determined.

System 110 may further be used to enhance the signal accuracy by providing a lock-in detection scheme which effectively takes the derivative of signal. As noted above, this lock-in detection improves the signal-to-noise ratio of the system, allowing for much greater accuracy. Lock-in processing is preferably implemented by processor 128. By dithering the beam energy and detecting output x-rays in synchronization with the beam, the system signal noise is greatly reduced.

Figure 8:
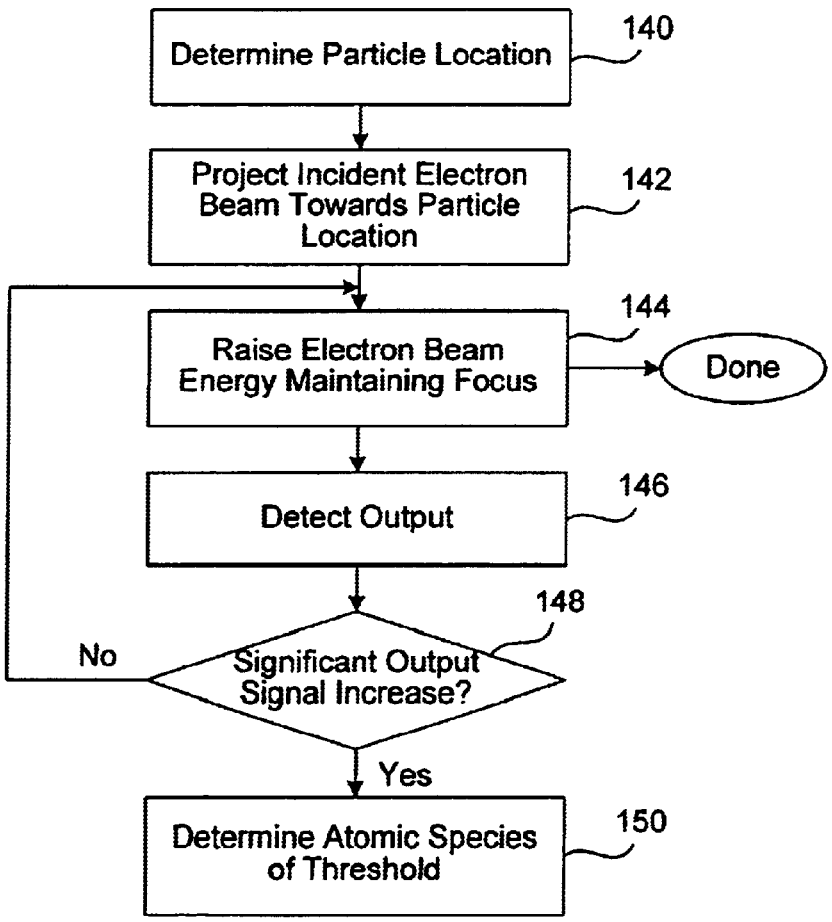
FIG. 8 is a flowchart describing the general steps of the present invention.

FIG. 8 describes general steps for using the technique of the present invention in relation to the diagram shown in FIG. 4. Step 140 determines the particle location 22. This step may be performed using any defect location system, of which many are presently available. In step 142, an incident electron beam 92 is projected toward particle location 22. The energy of incident electron beam 92 is varied over a range of energies in step 144. For most systems, the incident beam will be varied within a range of 1–5 keV. The incident beam is kept in focus on particle 22 while the energy of the beam is varied throughout this range.

The output signal 94 is detected by detector 96 in step 146. Step 148 detects a significant increase in intensity of the output signal, indicating that a threshold beam energy has been reached. The system determines the atomic species present in the particle from the threshold in step 150.

Figure 9:
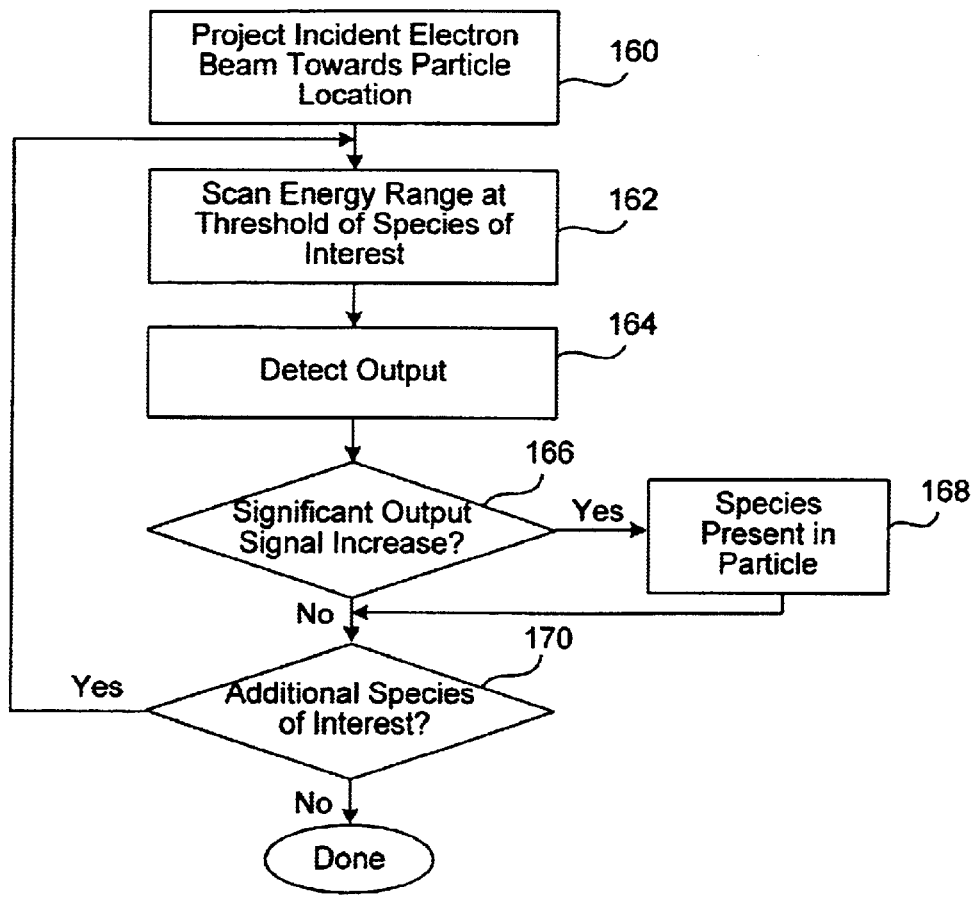
FIG. 9 is a flowchart describing the steps to identify a particular species of interest in a particle.

The steps in FIG. 9 may be used to identify particular species of interest in a particle. For example, in some situations the possible contaminants may be known—all that is needed is to isolate which element is present. Using the techniques of the present invention, the system can vary across very small ranges, e.g. 10 to 50 volts, corresponding to the threshold levels of possible species, rather than scanning across the entire possible range.

In step 160, the incident electron beam is projected towards a known particle location. Step 162 scans a small energy range around the threshold energy of a species of interest. For example, if Aluminum is suspected to be present in the defect particle, the scan range may be set to a 10–50 volt range centered at around 1.56 keV to detect for Aluminum.

In step 164, the output signal is detected. The output signal is monitored, and if a significant increase occurs in the output signal in step 166, the species may be determined to be present in the particle in step 168. If other species are suspected in step 170, additional energy ranges may be scanned to determine the composition of the particle.

Preferably, in the present invention the surface of the specimen retains a neutral charge while the analysis is taking place. As a result of the incident electron beam being projected towards specimen 12 as seen in FIG. 4, the surface of the substrate may build up an electrical charge due to captured or emitted electrons or ions, particularly for specimens of insulating materials. A variation in surface charge can affect the energy level of the electrons of the incident beam, skewing the resulting threshold values.

In order to neutralize charging on the specimen surface caused by the electron beam, a small quantity of gas 98, preferably provided as a jet, is produced as measurements are taken. The gas jet neutralizes the charge on the sample surface, holding the surface to a fixed potential that will not interfere with the accuracy of the measurements conducted in accordance with the present invention. Such gas neutralizing systems are known in the art. The gas is preferably a non-reactive gas, such as Argon or another noble element.

Figure 10:
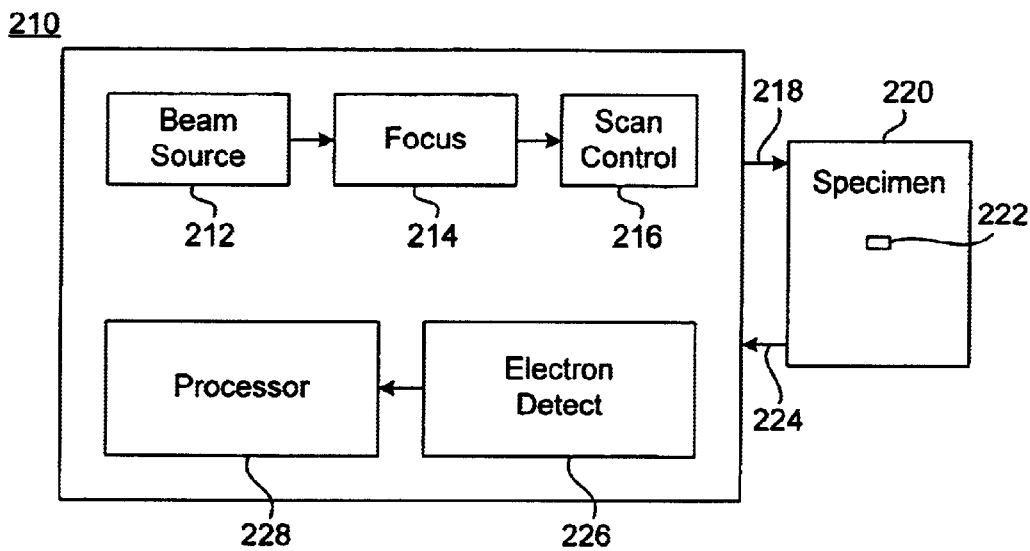
FIG. 10 shows a block diagram of an alternate embodiment of a system using the techniques of the present invention, employing electron detection.

The techniques of the present invention may also be useful to determine the chemical species of a particle using electron emission. FIG. 10 shows a block diagram of an alternative system 210 which uses electron detection. A beam source 212, a focusing means 214, and controller means 216 direct the scan of a variable energy, focused electron beam towards particular locations 222 on specimen 220. Electron detecting means 226 detects emitted electrons from specimen 220. In the system of the present invention, electron detecting means 226 may be a simple device which only senses an increase in electron emissions at any given incident beam energy. The emitted electron signal is processed by processor 228. The system of the present invention is far simpler and less expensive than conventional AES systems, because only the total electron yield needs to be measured. It is not necessary to resolve the energy of the Auger electrons. Resolving the energy of these electrons is a difficult task which requires expensive equipment and makes the system difficult to operate.

Electron beam 218 is projected by focus 214 and scan control 216 towards a defect location 222. The location of the defect may be determined by any of many well-known defect location techniques. Electron beam source 212 is a variable source that can be controlled over a wide range of energy levels. Focus control 214 must keep the beam in focus as it scans across energy levels. Focus control 214 may be implemented under computer control to keep beam 218 focused as it varies across a range of 0.5–20 keV, or even higher if so desired. However, a range of about 0.5 to about 5 keV is preferred.

Electron detecting means 226 must simply detect an increase in the total electron yield. It is not necessary that electron detecting means 226 resolve the output energy. The energy level of the incident beam is correlated by processor 228 with the output electron signal from electron detecting means 126. This information may be used to determine when the incident beam has reached a threshold energy level. By determining the energy level of each threshold, the chemical composition of the particle can be determined. Lock-in processing may be used, in a manner analogous to that described above for the x-ray system, to improve the signal to noise ratio.

In another embodiment of the invention, an area of the substrate including a plurality of pixels is concurrently analyzed. In this embodiment, an area of the substrate is exposed to an electron beam having a first known energy. Electrons emitted from the substrate are then detected, preferably by using an array of detectors. The array can be a linear array or a two dimensional array. Data derived from the electrons detected can then be used to produce a set of stored values which correspond to the quantity of electrons detected or rate of electron emission from each pixel in the area, at the first known incident electron energy. As in the preceding embodiments, the incident electron beam energy can then be varied to a second, preferably higher energy. Electrons emitted from the substrate are then detected, as in the preceding step. The steps of varying the energy and detecting the resulting emitted electrons can be repeated any number of desired times, over a range of energies of interest. The stored data values can then be processed, for example by subtraction on a pixel-by-pixel basis, to determine the change in emission of electrons from the substrate as a function of incident electron beam energy. As in the preceding embodiments, the incident energy at which the electron emission significantly changes for a given pixel may be used to determine the substrate composition at that pixel.

The detector can be used in a time delay integration mode, as described in more detail by Adler et al. in commonly owned, copending application Ser. No. 08/964,544, filed Nov. 5, 1997, now U.S. Pat. No. 5,869,833, and in U.S. Pat. No. 4,877,326 to Chadwick et al. In time delay integration mode, a plurality of detector elements are arranged in a two dimensional array. Electrons received by a first row of detector elements are transferred to a second row of detector elements, at a rate such that the transfer is synchronized with the relative movement between the substrate and the detector. Thus, as the pixels from the image move to the next row of detectors, the electrons from the exposure of the first row of detectors are also moved to the second row of detectors. The resulting accumulation of charge improves the quality of the detected signal, particularly when the rate at which electrons are emitted from the substrate is relatively low.

The composition of the substrate may be displayed in the form of a two dimensional image. The colors of the image may correspond to the elements present in the substrate. The image may be part of a graphic user interface, in which the user can use a pointing device to select a portion of an image of a substrate, and change the view (e.g., by enlarging the image at that point) or derive more information about the image, such as a graph of the raw data at that point which was used to identify the composition of the point.

In another embodiment of the invention, the incident electron beam can be scanned over a multipixel area of the substrate at a first energy. As the position of the beam is varied, pixel-by-pixel, over the area, the quantity of electrons emitted or rate of electron emission is determined at each pixel and the resulting data is stored in memory. The beam is then scanned again over at least a portion of the same area at a second energy, which is different from, and preferably higher than, the first energy. Emitted electrons are again detected and the resulting data is again stored. The process of scanning the area and producing data resulting from electrons detected during the scan is repeated as often as appropriate to cover a suitable range of incident energies. The resulting data is then processed to determine the composition of the substrate for one or more of said pixels.

Figure 11:
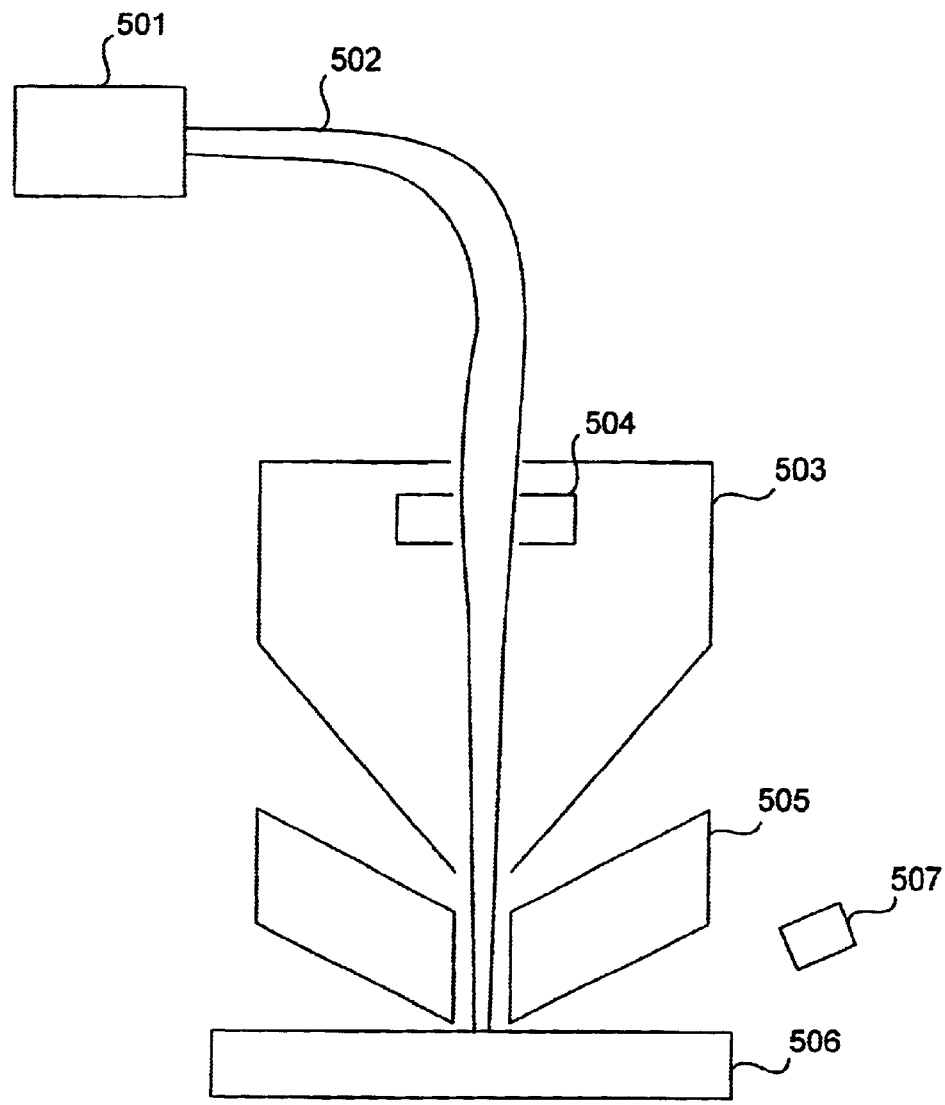
FIG. 11 shows a diagram of a system which can also sequentially produce both a first and second electron beam using an electron gun.

In order to reduce charging of the substrate, in one embodiment of the invention it is preferred to add a means for reducing the accumulation of charge. As shown in FIG. 11, source 501 can be an electron gun with a controllable voltage. The source 501 is caused to alternately emit electrons at high and low voltages. The high voltage corresponds the levels described in the preceding embodiments. The low voltage is somewhat (preferably 0.1 to 1.0 kV, and more preferably about 0.5 kV) lower than the high voltage. Thus, the resulting beam 502 of electrons will have relatively high energies when the source is at a high voltage, and relatively low energies when the source is at a low voltage. The energy of beam 502 is controlled by controlling the potential difference between the substrate 506 and the source 501. Accelerating/decelerating lens 503 is used to accelerate or decelerate the beam. The shape of the beam 502 is controlled using condenser/field lens 504. As the beam approaches substrate 506, its shape and energy are further controlled using objective lens 505. Detector 507 then detects light of any frequency, including x-rays, or electrons, emitted from substrate 506. For example, in an electron appearance spectroscopy system, detector 507 would detect x-rays. In an Auger system, detector 507 would detect electrons.

This system permits charging of substrate 506 to be controlled, because positive charge buildup on the surface of substrate 506 can be canceled by the low energy electrons. These electrons can be used to continuously remove positive charge on substrate as it is produced by the emission of secondary electrons. The energy of the electrons resulting from the lower voltage can be controlled such that they only strike the surface of substrate 506 when the substrate has a charge which is sufficiently positive to attract these electrons. If the substrate 506 has a neutral or negative charge, these electrons will not land on the surface.

Figure 12:
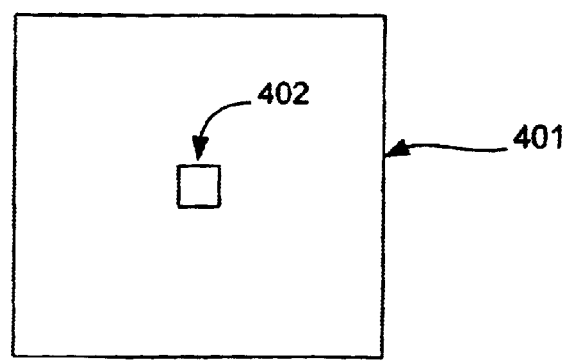
FIG. 12 shows a portion of a substrate exposed to two electron beams, such as those which may be produced by the system of FIG. 11.

As shown in FIG. 12, beam 306 covers a wide area 401 of the substrate when it is defocused and contains low energy electrons. Beam 306 is more tightly focused and directed only towards a feature contained at area 402 when it contains higher energy electrons.

The apparatus of FIG. 11 may be operated in a manner analogous to the system shown in commonly assigned co-pending U.S. patent application Ser. No. 08/784,749, filed Jan. 16, 1997, now U.S. Pat. No. 5,869,833, the complete disclosure of which is incorporated herein by reference. Other methods and systems described in said co-pending application may also (or alternatively) be employed herein for reduction or elimination of charge accumulation.

The methods of preventing charge buildup of a surface are useful not only in the spectroscopic methods described herein, but also in conventional spectroscopic methods such as Auger Electron Spectroscopy. Preventing charge buildup in Auger spectroscopy is important because Auger is a technique which is very sensitive to surface conditions, and the energy of the Auger electrons leaving the substrate surface can be affected by surface charge conditions.

EXAMPLE ONE

A silicon substrate having a plurality of semiconductor devices thereon is placed in an evacuated chamber. The pressure of the chamber is maintained at approximately $10^{-8}$ torr. The substrate is held on a stage by a chuck. A focused electron beam at a current of about one nA is directed towards a first predetermined location on the substrate. The beam is approximately 5 nm in diameter. The first location was found by an optical inspection of the substrate conducted before the substrate was placed in the chamber.

The elements of interest likely to be present at the first location include Si, C, Al and O. The beam energy is sequentially varied through a range of 50 Volts surrounding energy levels of 1.84 keV, 0.28 keV, 1.56 keV and 0.53 keV. These energy levels are chosen to correspond to those which are characteristic of the elements of interest. An increase in x-ray intensity is detected as the electron beam energy is varied through 1.84 keV, but not at any of the other energy levels. Therefore, the only element of interest present at the first predetermined location is Si.

The beam is then directed towards a second predetermined location, and the process described above is repeated at that location.

EXAMPLE TWO

A silicon substrate, similar to that described in Example One, is placed in an evacuated chamber. The pressure of the chamber is maintained at about $10^{-8}$ torr. A focused electron beam at a current of about 1 nA and having a diameter of about 5 nm is directed towards a first predetermined location on the substrate. The energy of the beam is initially set at about 0.1 keV and is gradually increased to about 5 keV over a time period of about one second while the focus of the beam is maintained on the first location.

The resulting x-ray emission intensity is detected by a lock-in scheme. Variations in the lock-in signal, produced at electron beam energies characteristic of known elements, are used to determine the elements present at the first location. Variations are detected in the lock-in signal at electron beam energies of 1.84 keV and 1.56 keV, and it is determined that Al and Si are present at the first location.

The beam is then directed towards a second predetermined location, and the process described above is repeated at that location.

EXAMPLE THREE

A silicon substrate containing non-conductive materials on an upper surface is placed in an evacuated chamber. The pressure of the chamber is maintained at about $10^{-4}$ torr of Argon gas, to neutralize charging at the surface of the nonconductive materials. A focused electron beam at a current of about 1 nA and having a diameter of about 5 nm is directed towards a first predetermined location on the substrate. The energy of the beam is initially set at about 0.1 keV and is gradually increased to about 5 keV over a time period of about one second while the focus of the beam is maintained on the first location.

The incident electron beam causes electrons to be emitted from the first location. The rate at which these electrons are emitted is detected and processed using a lock-in scheme. Variations in the lock-in signal, produced at electron beam energies characteristic of known elements, are used to determine the elements present at the first location. Variations are detected in the lock-in signal, and it is determined that C and Si are present at the first location.

The beam is then directed towards a second predetermined location, and the process described above is repeated at that location.

Although the invention has been described in relation to various implementations, together with modifications, variations, and extensions thereof, other implementations, modifications, variations and extensions are within the scope of the invention. Other embodiments may be apparent to those skilled in the art from consideration of the specification and invention disclosed herein. The invention is therefore not limited by the description contained herein or by the drawings, but only by the claims and their equivalents.

What is claimed is:

1. A method of determining the chemical composition of a feature on a substrate, comprising:
    a. directing a focused electron beam towards said feature, thereby causing said feature to emit x-rays;
    b. detecting said x-rays emitted from said feature, while varying the energy of said beam and maintaining the focus of said beam on said feature; and
    c. determining the composition of said feature.

2. The method of claim 1, wherein said electron beam is scanned over a surface of said substrate.

3. The method of claim 1, further comprising sequentially directing said focused electron beam towards each of a plurality of features on said substrate, sequentially detecting x-rays emitted from each of said features while varying the energy of said beam, and determining the composition of each of said features.

4. The method of claim 1, wherein said composition of said feature is determined by monitoring the relative intensity of said x-rays while varying the energy of said beam.

5. The method of claim 4, wherein said energy is gradually increased while said x-rays are detected.

6. The method of claim 1, wherein said composition of said feature is determined from a lock-in or other averaged signal corresponding to a derivative of the intensity of said x-rays with respect to beam energy.

7. The method of claim 1, wherein said feature is a defect.

8. The method of claim 7, wherein said defect is at a predetermined location on said substrate.

9. The method of claim 1, wherein said beam is sequentially varied through predetermined energy levels, said predetermined energy levels being selected to produce an increase in x-ray emission intensity from known materials.

10. The method of claim 1, further comprising maintaining said substrate at a substantially constant voltage while said substrate is exposed to said electron beam.

11. The method of claim 10, wherein said substrate is maintained at said substantially constant voltage by a gas jet directed at said substrate.

12. The method of claim 10, wherein said substantially constant voltage is approximately zero volts with respect to a predefined reference voltage.

13. The method of claim 1, wherein said beam is stepped over the surface of said substrate to locations corresponding substantially to predetermined defect sites on said substrate.

14. The method of claim 4, wherein the energy of said beam is varied step-wise through predetermined energy levels.

15. A method for determining the chemical composition of a feature, comprising:
    a. directing a focused electron beam towards said feature, said electron beam having a predetermined energy corresponding to a value which causes an element to emit x-rays;
    b. detecting x-rays emitted from said feature, while varying the energy of said beam in a range around said predetermined energy and while maintaining the focus of said beam on said feature; and
    c. determining the composition of said feature.

16. A method of determining the chemical composition of a feature on a substrate, comprising:
   a. directing a focused electron beam towards said feature, thereby causing said feature to emit electrons;
   b. detecting said electrons emitted from said feature, while varying the energy of said beam and maintaining the focus of said beam on said feature; and
   c. determining the composition of said feature.

17. The method of claim 16, wherein said electron beam is scanned over a surface of said substrate.

18. The method of claim 16, further comprising sequentially directing said focused electron beam towards each of a plurality of features on said substrate, sequentially detecting electrons emitted from each of said features while varying the energy of said beam, and determining the composition of each of said features.

19. The method of claim 16, wherein said composition of said feature is determined by monitoring the relative intensity of said electrons while varying the energy of said beam.

20. The method of claim 19, wherein said energy is gradually increased while said electrons are detected.

21. The method of claim 16, wherein said composition of said feature is determined from a lock-in signal corresponding to a derivative of the intensity of said electrons.

22. The method of claim 16, wherein said feature is a defect.

23. The method of claim 22, wherein said defect is at a predetermined location on said substrate.

24. The method of claim 16, wherein said beam is sequentially varied through predetermined energy levels, said predetermined energy levels being selected to produce an increase in electron emission intensity from known materials.

25. The method of claim 16, further comprising maintaining said substrate at a substantially constant voltage while said substrate is exposed to said electron beam.

26. The method of claim 25, wherein said substrate is maintained at said substantially constant voltage by a gas jet directed at said substrate.

27. The method of claim 25, wherein said substantially constant voltage is about zero volts.

28. The method of claim 16, wherein said beam is stepped over the surface of said substrate to locations corresponding substantially to predetermined defect sites on said substrate.

29. The method of claim 19, wherein the energy of said beam is varied step-wise through predetermined energy levels.

30. A method for determining the chemical composition of a feature, comprising:
   a. directing a focused electron beam towards said feature, said electron beam having a predetermined energy corresponding to a value which causes an element to emit electrons;
   b. detecting electrons emitted from said feature, while varying the energy of said beam in a range around said predetermined energy and while maintaining the focus of said beam on said feature; and
   c. determining the composition of said feature.

31. An apparatus for determining the chemical composition of a feature on a substrate, comprising:
   a. a focused electron beam directed towards said feature, said beam having an energy sufficient to cause said feature to emit x-rays;
   b. a detector for detecting said x-rays emitted from said feature, while varying the energy of said beam and maintaining the focus of said beam on said feature; and
   c. a processor for determining the composition of said feature.

32. The apparatus of claim 31, further comprising a gas source directed at said substrate for maintaining said substrate at a substantially constant voltage.

33. The apparatus of claim 31, further comprising a variable energy electron beam source for producing said electron beam and a controller for controlling the energy of said beam.

34. An apparatus for determining the chemical composition of a feature on a substrate, comprising:
   a. a focused electron beam directed towards said feature, said beam having an energy sufficient to cause said feature to emit electrons;
   b. a detector for detecting said electrons emitted from said feature, while varying the energy of said beam and maintaining the focus of said beam on said feature; and
   c. a processor for determining the composition of said feature.

35. The apparatus of claim 34, further comprising a gas source directed at said substrate for maintaining said substrate at a substantially constant voltage.

36. The apparatus of claim 34, further comprising a variable energy electron beam source for producing said electron beam and a controller for controlling the energy of said beam.

37. The apparatus of claim 34, further comprising a chamber for holding said sample in a vacuum.

38. The apparatus of claim 34, wherein said detector is a lock-in detector.

39. The apparatus of claim 34, further comprising a CRT screen for viewing an image of said feature.

40. The apparatus of claim 31, wherein said detector includes a scintillator.

41. The apparatus of claim 34, wherein said detector includes a channeltron.

42. An apparatus for determining the chemical composition of a feature on a substrate, comprising:
   a. means for directing a focused electron beam towards said feature, thereby causing said feature to emit x-rays;
   b. means for detecting said x-rays emitted from said feature, while varying the energy of said beam and maintaining the focus of said beam on said feature; and
   c. means for determining the composition of said feature.

43. An apparatus for determining the chemical composition of a feature on a substrate, comprising:
   a. means for directing a focused electron beam towards said feature, thereby causing said feature to emit electrons;
   b. means for detecting said electrons emitted from said feature, while varying the energy of said beam and maintaining the focus of said beam on said feature; and
   c. means for determining the composition of said feature.

44. A method for determining the chemical composition of a surface, comprising:
   a. exposing said surface to a first set of electrons in a beam, said first set of electrons having energies within a first range selected for energizing said surface to perform a spectroscopic analysis of said surface and determine said chemical composition; and
   b. exposing said surface to a second set of electrons in a beam, said second set of electrons having energies within a second range, different from said first range, wherein said second range of energies is predetermined to provide electrons from said second set which land on said surface to reduce charging of said surface.

45. The method of claim 44, wherein said surface is alternately exposed to said first set of electrons and said second set of electrons.

46. The method of claim 44, wherein said spectroscopic analysis is Auger electron spectroscopy.

47. The method of claim 44, wherein said second set of electrons is provided in the form of a defocused beam.

48. The method of claim 47, wherein said defocused beam is incident on said substrate over a larger area than an area of said substrate over which said first beam is incident.

49. The method of claim 44, further comprising exposing said surface to an inert gas.

50. The method of claim 49, wherein said inert gas comprises positive ions, and wherein said ions land on said surface and carry away excess negative charge from said surface.

51. The method of claim 4, wherein said composition is determined by finding one or more energies of said beam at which a change in the emission of x-rays is detected, said one or more energies corresponding to energies characteristic of atomic elements present in said feature.

* * * * *